(12) United States Patent
Yam et al.

(10) Patent No.: US 8,415,473 B2
(45) Date of Patent: *Apr. 9, 2013

(54) LUMINESCENT GOLD(III) COMPOUNDS FOR ORGANIC LIGHT-EMITTING DEVICES AND THEIR PREPARATION

(75) Inventors: Vivian Wing-Wah Yam, Hong Kong (CN); Vonika Ka-Man Au, Hong Kong (CN); Mei-Yee Chan, Hong Kong (CN); Keith Man-Chung Wong, Hong Kong (CN); Hoi-Sing Kwok, Hong Kong (CN)

(73) Assignee: Versitech Limited, Hong Kong (CN)

( * ) Notice: Subject to any disclaimer, the term of this patent is extended or adjusted under 35 U.S.C. 154(b) by 460 days.

This patent is subject to a terminal disclaimer.

(21) Appl. No.: 12/494,765

(22) Filed: Jun. 30, 2009

(65) Prior Publication Data

US 2009/0278453 A1    Nov. 12, 2009

Related U.S. Application Data

(63) Continuation-in-part of application No. 10/977,200, filed on Oct. 29, 2004, now Pat. No. 7,572,912.

(51) Int. Cl.
*C07F 1/12* (2006.01)
*H01L 51/50* (2006.01)

(52) U.S. Cl. ............. 546/2; 428/690; 428/917; 313/504

(58) Field of Classification Search ...... 546/2; 428/690, 428/917; 313/504
See application file for complete search history.

(56) References Cited

U.S. PATENT DOCUMENTS 7,572,912 B2 * 8/2009 Yam et al. ......................... 546/2

* cited by examiner

*Primary Examiner* — Charanjit Aulakh
(74) *Attorney, Agent, or Firm* — Saliwanchik, Lloyd & Eisenschenk

(57) ABSTRACT

A class of luminescent gold(III) compounds containing a tridentate ligand with one strong σ-donating group having the chemical structure depicted by generic formula (I):

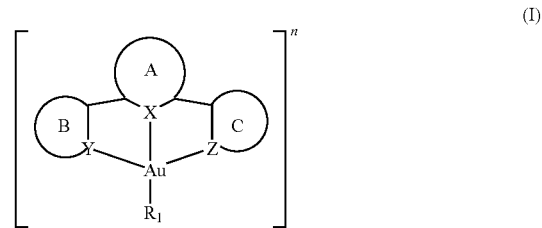

wherein:
(a) X is selected from nitrogen;
(b) Y and Z selected from carbon;
(c) A is cyclic structure derivative of pyridine group;
(d) B and C are cyclic structure derivative of phenyl groups;
(e) $R_1$ is an optionally substituted carbon donor ligand attached to the gold atom;
(f) n is zero, a positive integer or a negative integer.

21 Claims, 5 Drawing Sheets

LUMINESCENT GOLD(III) COMPOUNDS FOR ORGANIC LIGHT-EMITTING DEVICES AND THEIR PREPARATION

CROSS-REFERENCE TO RELATED APPLICATION

This application is a continuation in part of U.S. application Ser. No. 10/977,200, filed Oct. 29, 2004 now U.S. Pat. No. 7,572,912, which is hereby incorporated by reference in its entirety.

FIELD OF THE INVENTION

The present invention is related to the design and synthesis of novel classes of gold(III) compounds containing a tridentate ligand with one strong σ-donating group. Such compounds can be used as light-emitting material in phosphorescence-based organic light-emitting devices (OLEDs).

BACKGROUND

In recent years, much attention has been drawn towards the research and development of organic light-emitting devices. Such enormous increase in research interest is highly correlated to the potential application of OLEDs in commercial flat panel displays. With the advantages of low cost, light weight, low operating voltage, high brightness, robustness, color tunability, wide viewing angle, ease of fabrication onto flexible substrates as well as low energy consumption, OLEDs are considered as remarkably attractive candidates for flat panel display technologies.

Typically an OLED contains several layers of semiconductor sandwiched between two electrodes. The cathode is composed of a low work function metal alloy deposited by vacuum evaporation, whereas the anode is a transparent conductor such as indium tin oxide (ITO). Upon the application of a DC voltage, holes injected by the ITO electrode and electrons injected by the metal electrode will recombine to form excitons. Subsequent relaxation of excitons will then result in the generation of electroluminescence (EL).

In order to achieve higher OLED performance, multiple organic semiconductor layers can be incorporated to further separate the two electrodes. There are two main categories of these semiconductor layers, namely vacuum-deposited small molecules and spin-coated polymeric materials. Both fabrication methods have their respective advantages. Vacuum deposition can allow better control over layer thickness and uniformity, while spin coating offers the ease of use and lower production cost [Burrows, P. E.; Forrest, S. R.; Thompson, M. E. *Current Opinion in Solid State and Materials Science*, 236 (1997)].

In spite of the fact that electroluminescence from organic polymers was initially reported in the 1970s [Kaneto, K.; Yoshino, K.; Koa, K.; Inuishi, Y. *Jpn. J. Appl. Phys.* 18, 1023 (1974)], it was only after the report on yellow-green electroluminescence from poly(p-phenylenenvinylene) (PPV) that light-emitting polymers and OLEDs have received much attention [Burroughs, J. H.; Bradley, D. D. C.; Brown, A. R.; Marks, N.; Friend, R. H.; Burn, P. L.; Holmes, A. B. *Nature* 347, 539 (1990)]. Later on, similar studies were reported by using PPV derivatives as the light-emitting polymers [Braun, D.; Heeger, A. *J. Appl. Phys. Lett.* 58, 1982 (1991)]. Since then a number of new electroluminescent polymers have been investigated for improved properties.

Electroluminescence of organic materials was discovered in anthracene crystals immersed in liquid electrolyte in 1965 [Helfruch, W.; Schneider, W. G. *Phys. Rev. Lett.* 14, 229 (1965)]. Although lower operating voltages could be achieved by using a thin film of anthracene as well as solid electrodes, very low efficiency of such a single-layer device was encountered. High-performance green electroluminescence from an organic small molecule, aluminum tris(quinolate) ($Alq_3$), was first reported in 1987 [Tang, C. W.; VanSlyke, S. A. *Appl. Phys. Lett.* 51, 913 (1987)]. A double-layer OLED with high efficiency and low operating voltage was described, in which $Alq_3$ was utilized both as emitting layer and electron transporting layer. Subsequent modifications of the device with triple-layer structure gave better performance with higher efficiency.

For best performance of phosphorescence-based OLEDs, it is desirable for the semiconducting materials to have short lifetimes. One way is to mix singlet and triplet excited states by making use of spin-orbit (L-S) coupling. In the presence of a heavy metal center, the chance of spin-orbit coupling can be greatly enhanced. Hence, the use of heavy metal complexes in OLEDs is preferred over purely organic materials, in which the lowest energy excited state of an organometallic compound is commonly a metal-to-ligand charge transfer (MLCT) triplet state, mixed with the excited singlet state through L-S coupling, so as to obtain higher photoluminescence efficiencies [Baldo, M. A.; Thompson, M. E.; Forrest, S. R. *Pure Appl. Chem.* 71, 2095 (1999)]. In 1998, Baldo et al. demonstrated a phosphorescence electroluminescence device with high quantum efficiency by using platinum(II) 2,3,7,8,12,13,17,18-octaethyl-21H,23H-porphine (PtOEP) as a dye [Baldo, M. A.; O'Brien, D. F.; You, Y.; Shoustikow, A.; Sibley, S.; Thompson, M. E.; Forrest, S. R. *Nature* 395, 151 (1998)]. A multilayer device in which the emitting layer of $Alq_3$ is doped with PtOEP showed a strong emission at 650 nm attributed to the triplet excitons of PtOEP. Cyclometalated iridium(III) is known to show phosphorescence and is another class of materials used for high efficiency OLEDs. Baldo et al. reported the use of fac-tri(2-phenylpyridine)iridium(III) [Ir(ppy)$_3$] as phosphorescence emitting material which was doped in 4,4'-N,N'-diarbazole-biphenyl (CBP) as a host in an OLED to give high quantum efficiency [Baldo, M. A.; Lamansky, S.; Burrows, P. E.; Thompson, M. E.; Forrest, S. R. *Appl. Phys. Lett.* 75, 4 (1999)]. In addition, fac-tri-(phenylpyridine)iridium(III) [Ir(ppy)$_3$] was used as phosphorescence sensitizer for high efficiency fluorescent OLED [Baldo, M. A.; Thompson, M. E.; Forrest, S. R. *Nature*, 403, 750 (2000)]. Using the concept of a phosphorescence emitter with a higher population of excitons, very high efficiency red fluorescence from [2-methyl-6-[2-(2,3,6,7-tetrahydro-1H,5H-benzo[H]quinolizin-9-yl)-ethenyl]-4H-pyran-4-ylidene]propanedinitrile (DCM2) was found in a multilayer OLED composed of Ir(ppy)$_3$ and DCM2 dopant layers. In a sensitization process, energy is transferred from Ir(ppy)$_3$ to DCM2 to give such high efficiency fluorescence.

Apart from the enhancement of the emission efficiency, the ability to bring about a variation in the emission color would be important. Most of the common approaches involve the use of different emission characteristics for color tuning. Examples that employ a single light-emitting material as dopant to generate more than one emission color have been rare. Recent studies have shown that different emission colors from a single emissive dopant could be generated by using phosphorescent material through a change in the direction of the bias or in the dopant concentration. Welter et al. reported the fabrication of a simple OLED consisting of semiconducting polymer PPV and phosphorescent ruthenium polypyridine dopant [Welter, S.; Krunner, K.; Hofstraat, J. W.; De Cola, D. *Nature*, 421, 54 (2003)]. At forward bias, red emission from the excited state of the phosphorescent ruthenium polypyridine dopant was observed, while the OLED emitted a green emission at reverse bias in that the lowest excited singlet state of PPV was populated. Adanmovich et al. reported the use of a series of phosphorescent platinum(II) [2-(4,6-difluorophenyl)pyridinato-N,C$^{2'}$] β-diketones as single emissive dopant in OLED [Adamovich, V.; Brooks, J.; Tamayo, A.; Alexander, A. M.; Djurovich, P. R.; D'Andrade, B. W.; Adachi, C.; Forrest, S. R.; Thompson, M. E. *New J. Chem.* 26, 1171 (2002)]. Both blue emission from monomeric species and orange emission from the aggregates were observed in such OLED and the relative intensity of the orange emission increases as the doping level is increased. As a result, the electroluminescence color can be tuned by changing the dopant concentration with equal intensities of the monomeric and aggregate bands. In both cases, the change of electroluminescence color in OLED can be accomplished upon a variation of the external stimulus or fabrication conditions while keeping the light-emitting material the same.

Even though there has been an increasing interest in electrophosphorescent materials, particularly metal complexes with heavy metal centers, most of the work has been focused on the use of iridium(III), platinum(II) and ruthenium(II), whereas the use of other metal centers have been much less explored. In contrast to the isoelectronic platinum(II) compounds which are known to show rich luminescence properties, very few examples of luminescent gold(III) complexes have been reported, probably due to the presence of low-energy d-d ligand field (LF) states and the electrophilicity of the gold(III) metal center. One way to enhance luminescence of gold(III) complexes is through the introduction of strong σ-donating ligands, which was first demonstrated by Yam et al. in which stable gold(III) aryl compounds were synthesized and found to display interesting photoluminescence properties even at room temperature [Yam, V. W. W.; Choi, S. W. K.; Lai, T. F.; Lee, W. K. *J. Chem. Soc., Dalton Trans.* 1001 (1993)]. Another interesting donor ligand is the alkynyl group. Although the luminescence properties of gold(I) alkynyls have been extensively studied, the chemistry of gold(III) alkynyls has been essentially ignored, except for a brief report on the synthesis of an alkynylgold(III) compound of 6-benzyl-2,2'-bipyridine in the literature [Cinellu, M. A.; Minghetti, G.; Pinna, M. V.; Stoccoro, S.; Zucca, A.; Manassero, M. *J. Chem. Soc. Dalton Trans* 2823 (1999)], but their luminescence behaviour has remained totally unexplored. Yam et al. later synthesized a series of bis-cyclometalated alkynylgold(III) compounds using various strong σ-donating alkynyl ligands, and all these compounds were found to exhibit rich luminescence behaviors at both room and low temperatures in various media [Yam, V. W.-W.; Wong, K. M.-C.; Hung, L.-L.; Zhu, N. *Angew. Chem. Int. Ed.* 44, 3107 (2005); Wong, K. M.-C.; Hung, L.-L.; Lam, W. H.; Zhu, N.; Yam, V. W.-W. *J. Am. Chem. Soc.* 129, 4350 (2007); Wong, K. M.-C.; Zhu, X.; Hung, L.-L.; Zhu, N.; Yam, V. W.-W.; Kwok, H. S. *Chem. Commun.* 2906 (2005)]. The present inventors have described herein the design, synthesis and photoluminescence behaviours of luminescent gold(III) compounds with at least one strong σ-donating group, and the use of these compounds as electrophosphorescent material in OLEDs to give strong electroluminescence with high efficiency.

BRIEF SUMMARY

The present invention is directed to novel luminescent cyclometalated gold(III) compounds, their preparation, and OLEDs containing them. Described below is a report of the design and synthesis of various novel gold(III) compounds.

The objective of the present invention is to provide a novel class of cyclometalated gold(III) compounds for applications in organic light-emitting devices. The invented gold(III) compound is a coordination compound that contains a cyclometalated ligand and at least one strong σ-donating group, both coordinated to a gold(III) metal center. Likewise, any σ-donating group can be employed as the ancillary ligand, for instance, alkynyl groups.

The compounds have the chemical structure shown in generic formula (I),

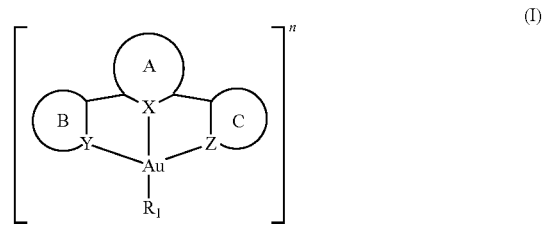

wherein:
(a) X is selected from nitrogen;
(b) Y and Z selected from carbon;
(c) A is cyclic structure derivative of pyridine group;
(d) B and C are cyclic structure derivative of phenyl groups;
(e) R$_1$ is an optionally substituted carbon donor ligand attached to the gold atom;
(f) n is zero, a positive integer or a negative integer.

It is expected that the luminescent gold(III) compounds of the present invention will show strong photoluminescence via triplet excited state upon photo-excitation, or electroluminescence via triplet exciton upon applying a DC voltage. Such luminescence properties are observed in compounds that have been synthesized. Preferred compounds of the invention are thermally stable and volatile enough to be able to form a thin layer by sublimation or vacuum deposition. Alternatively, the compounds can be doped into a host matrix for thin film deposition by spin-coating or inkjet printing or other known fabrication methods.

The present invention is also directed to the use of luminescent compounds of general formula (I) as phosphorescent emitters or dopants for the fabrication of OLEDs to generate electroluminescence. Some examples of this class of compounds are illustrated in the present invention for the fabrication of OLEDs with improved current and power efficiencies.

In an OLED according to the present invention, the luminescent gold(III) compound is included in a light-emitting layer. The typical structure of an OLED using luminescent compounds of the present invention as a light-emitting layer is in the order shown in FIG. 1: cathode/electron transporting layer/luminescent gold(III) compound as a light-emitting layer/carrier refinement layer/hole transporting layer/anode.

DETAILED DESCRIPTION

Figure 1:
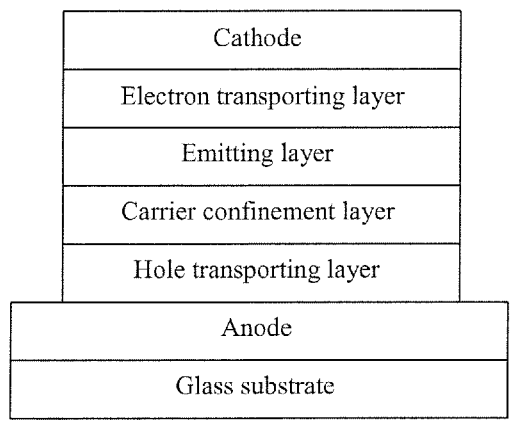
FIG. 1 is a schematic diagram of the basic structure of an organic EL device.

The present invention is directed to the synthesis and luminescence studies of a class of luminescent gold(III) compounds with one tridentate ligand and one strong σ-donating group; and the use of such compounds as light-emitting material in OLEDs to provide electroluminescence with high efficiency and brightness. The compounds have the chemical structure shown in generic formula (I),

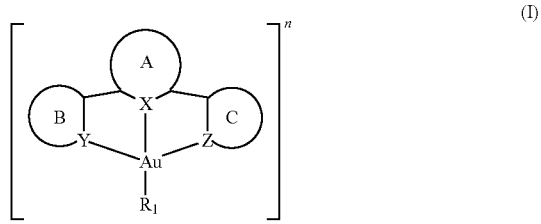

wherein:
(a) X is selected from nitrogen;
(b) Y and Z selected from carbon;
(c) A is cyclic structure derivative of pyridine group;
(d) B and C are cyclic structure derivative of phenyl groups;
(e) $R_1$ is an optionally substituted carbon donor ligand attached to the gold atom;
(f) n is the charge on the compound and is zero for a neutral compound or can be a positive integer or a negative integer where the compound is the cation or anion, respectively, of a salt. $R_1$ is selected from, but is not limited to, alkylalkynyl, substituted alkylalkynyl, arylalkynyl, substituted arylalkynyl, heteroarylalkynyl and substituted heteroarylalkynyl.

Ring A is pyridine or pyridyl derivative, but is not limited to, with one or more alkyl, alkenyl, alkynyl, alkylaryl, cycloalkyl, OR, $NR_2$, SR, C(O)R, C(O)OR, C(O)$NR_2$, CN, $CF_3$, $NO_2$, $SO_2$, SOR, $SO_3R$, halo, aryl, substituted aryl, heteroaryl, substituted heteroaryl or heterocyclic group. Rings B and C are benzene or phenyl derivatives, but are not limited to, with one or more alkyl, alkenyl, alkynyl, alkylaryl, cycloalkyl, OR, $NR_2$, SR, C(O)R, C(O)OR, C(O)$NR_2$, CN, $CF_3$, $NO_2$, $SO_2$, SOR, $SO_3R$, halo, aryl, substituted aryl, heteroaryl, substituted heteroaryl or heterocyclic group.

In the present disclosure the following terms are used.

The term "optional" or "optionally" means that the subsequently described event or circumstance may or may not occur, and that the description includes instances where said event or circumstance occurs and instances in which it does not. For example, "optionally substituted alkyl" includes "alkyl" and "substituted alkyl," as defined below.

The term "halo" or "halogen" as used herein includes fluorine, chlorine, bromine and iodine. The term "alkyl" as used herein includes straight and branched chain alkyl groups, as well as cycloalkyl group with cyclic structure of alkyl groups. Preferred alkyl groups are those containing from one to eighteen carbon atoms and includes methyl, ethyl, propyl, isopropyl, butyl, isobutyl, tert-butyl, and the like. In addition, the alkyl group may be optionally substituted with one or more substituents selected from OR, $NR_2$, SR, C(O)R, C(O)OR, C(O)$NR_2$, CN, $CF_3$, $NO_2$, $SO_2$, SOR, $SO_3R$, halo and cyclic-amino.

The term "alkenyl" as used herein includes both straight and branched chain alkene radicals. Preferred alkenyl groups are those containing two to eighteen carbon atoms. In addition, the alkenyl group may be optionally substituted with one or more substituents selected from OR, $NR_2$, SR, C(O)R, C(O)OR, C(O)$NR_2$, CN, $CF_3$, $NO_2$, $SO_2$, SOR, $SO_3R$, halo and cyclic-amino. The term "alkynyl" as used herein includes both straight and branched chain alkyne radicals. Preferred alkynyl groups are those containing two to eighteen carbon atoms. In addition, the alkynyl group may be optionally substituted with one or more substituents selected from OR, $NR_2$, SR, C(O)R, C(O)OR, C(O)$NR_2$, CN, $CF_3$, $NO_2$, $SO_2$, SOR, $SO_3R$, halo and cyclic-amino.

The term "arylalkynyl" as used herein includes an alkynyl group which has an aromatic group as a substituent. In addition, the arylalkynyl group may be optionally substituted with one or more substituents selected from OR, $NR_2$, SR, C(O)R, C(O)OR, C(O)$NR_2$, CN, $CF_3$, $NO_2$, $SO_2$, SOR, $SO_3R$, halo and cyclic-amino.

The term "alkylaryl" as used herein includes an alkyl group which has an aromatic group as a substituent. In addition, the alkylaryl group may be optionally substituted with one or more substituents selected from OR, $NR_2$, SR, C(O)R, C(O)OR, C(O)$NR_2$, CN, $CF_3$, $NO_2$, $SO_2$, SOR, $SO_3R$, halo and cyclic-amino.

Preferred alkyl groups are $C_1$ through $C_{18}$ alkyls. Similarly $C_1$ through $C_{18}$ alkoxy and aryl groups are preferred. $C_1$ through $C_{18}$ heteroaryl, alkylamino, arylamino, alkylsulfido, arylsulfido, alkylphosphino or arylphosphino groups are preferable.

Aryl alone or in combination includes carbocyclic aromatic systems. The systems may contain one, two or three rings wherein each ring may be attached together in a pendent manner or may be fused. Preferably the rings are 5- or 6-membered rings. Aryl groups include, but are not exclusive to, unsubstituted or substituted derivatives of benzene, naphthylene, pyrene, anthracene, pentacene, benzo[a]pyrene, chrysene, coronene, corannulene, naphthacene, phenanthrene, triphenyklene, ovalene, benzophenanthrene, perylene, benzo[ghi]perylene, antanthrene, pentaphene, picene, dibenzo[3,4;9,10]pyrene, benzo[3,4]pyrene, dibenzo[3,4;8,9]pyrene, dibenzo[3,4;6,7]pyrene, dibenzo[1,2;3,4]pyrene, and naphto[2,3;3,4]pyrene; wherein the positions of attachment and substitution can be at any carbon of the group that does not sterically inhibit formation of compound of formula (I), as can be appreciated by one skilled in the art. Preferred substituents include but are not limited to alkyl, alkoxy, aryl.

Heteroaryl alone or in combination includes heterocyclic aromatic systems. The systems may contain one, two or three rings wherein each ring may be attached together in a pendent manner or may be fused. Preferably the rings are 5- or 6-membered rings. Heterocyclic and heterocycle refer to a 3 to 7-membered ring containing at least one heteroatom. Heteroaryl groups include, but are not exclusive to, unsubstituted or substituted derivatives of pyridine, thiophene, furan, pyrazole, imidazole, oxazole, isoxazole, thiazole, isothiazole, pyrrole, pyrazine, pyridazine, pyrimidine, benzimidazole, benzofuran, benzothiazole, indole, triazole, tetrazole, pyran, thiapyran, oxadiazole, triazine, tetrazine, carbazole, dibenzothiophene, dibenzofuran, isoindole, quinoline, isoquinoline, chromene, isochromene and non-aromatic rings including but not limited to piperazine, piperidine, and pyrrolidine; wherein the position of attachment or substitution can be at any carbon of the group that does not sterically inhibit formation of compound of formula (I), as can be appreciated by one skilled in the art. Preferred substituents include but are not limited to alkyl, alkoxy, aryl.

Heteroatom refers to S, O, N, P.

The cyclic structure derivative of pyridine group A is attached at the 2 and 6 position of the pyridine ring to B and C. The group A can be substituted in the 3, 4 or 5 positions. Appropriate substituents at the 3 and 4 are those of appropriate size to allow simultaneous bonding of rings A, B and C. B and C are cyclic structure derived from phenyl groups and can be substituted in any manner that permits simultaneous Au—C and Au—N bonds between the Au atom and A, B, C and $R_1$ of compound (I). B and C can be polycyclic aromatics, such as naphthyl units, for example. The rings A and B can be combined as a pyridine and a phenyl derived portion of a polycyclic heteroaromatic structure. For example A and B can be provided from, for example, 7,8-benzoquinoline or other polycyclic heteroaromatic where appropriate chemical bonding to the Au atom permits formation of the gold(III) compound (I). In like manner all three rings, A, B and C, can be provided from, for example, dibenz[c,h]acridine or other polycyclic heteroaromatic where appropriate chemical bonding to the Au atom permits formation of the gold(III) compound (I).

Substituted refers to any level of substitution. Mono-, di- and tri-substitutions are readily prepared. Substituents including hydrogen, halogen, aryl, alkyl and heteroaryl are readily prepared.

Cyclometalated ligand is a term well known in the art and includes but is not limited to 2,6-diphenylpyridine (C^N^C), 2,6-bis(4-tert-butylphenyl)pyridine ($^t$BuC^N^C$^t$Bu) and 2,6-diphenyl-4-(2,5-difluorophenyl)pyridine (2,5-F$_2$-Ph-C^N^C), 2,6-diphenyl-4-p-tolylpyridine (C^NTOl^C), 2,6-diphenyl-4-phenylpyridine (C^NPh^C), 2,6-bis(4-fluorophenyl)pyridine (FC^N^CF), 2,6-diphenyl-4-(4-isopropylphenyl)pyridine (4-$^i$Pr-Ph-C^N^C), 2,6-diphenyl-4-(4-nitrophenyl)pyridine(4-NO$_2$-Ph-C^N^C), 2,6-diphenyl-4-(4-methoxyphenyl)pyridine (4-OMe-Ph-C^N^C), 2,6-diphenyl-4-(4-methylphenyl)pyridine (4-Me-Ph-C^N^C), 2,6-diphenyl-4-(4-ethylyphenyl)-pyridine (4-Et-Ph-C^N^C), 2,6-diphenyl-4-(2,3,4-trimethoxyphenyl)pyridine (2,3,4-OMe$_3$-Ph-C^N^C), 2,6-bis(4-methoxyphenyl)-4-(4-nitrophenyl)pyridine (4-NO$_2$-Ph-MeOC^N^COMe), 2,6-bis(2,4-dichlorophenyl)-4-(4-isopropylphenyl)-pyridine (4-$^i$Pr-Ph-Cl$_2$C^N^CCl$_2$), 2,6-diphenyl-4-(4-tosylphenyl)pyridine (4-OTs-Ph-C^N^C), 2,6-diphenyl-4-(4-dimethylaminophenyl)pyridine (4-NMe$_2$-Ph-C^N^C), 2,6-diphenyl-4-(4-diphenylaminophenyl)pyridine (4-NPh$_2$-Ph-C^N^C), 2,6-diphenyl-4-(4-bromophenyl)pyridine (4-Br-Ph-C^N^C), 2,6-diphenyl-4-(4-chlorophenyl)pyridine (4-Cl-Ph-C^N^C), 2,6-diphenyl-4-(4-fluorophenyl)pyridine (4-F-Ph-C^N^C), 2,6-diphenyl-4-(4-iodophenyl)pyridine (4-I-Ph-C^N^C), 2,6-diphenyl-4-(2,5-dimethylphenyl)pyridine (2,5-Me$_2$-Ph-C^N^C), 2,6-diphenyl-4-(2,3,4,5,6-pentafluorophenyl) pyridine (2,3,4,5,6-F$_5$-Ph-C^N^C).

Benzene includes substituted or unsubstituted benzene.
Pyridine includes substituted or unsubstituted pyridine.
Thiophene includes substituted or unsubstituted thiophene.
Furan includes substituted or unsubstituted furan.
Pyrazole includes substituted or unsubstituted pyrazole.
Imidazole includes substituted or unsubstituted imidazole.
Oxazole includes substituted or unsubstituted oxazole.
Isoxazole includes substituted or unsubstituted isoxazole.
Thiazole includes substituted or unsubstituted thiazole.
Isothiazole includes substituted or unsubstituted isothiazole.
Pyrrole includes substituted or unsubstituted pyrrole.
Pyrazine includes substituted or unsubstituted pyrazine.
Pyridazine includes substituted or unsubstituted pyridazine.
Pyrimidine includes substituted or unsubstituted pyrimidine.
Benzimidazole includes substituted or unsubstituted benzimidazole.
Benzofuran includes substituted or unsubstituted benzofuran.
Benzothiazole includes substituted or unsubstituted benzothiazole.
Indole includes substituted or unsubstituted indole.
Naphthalene includes substituted or unsubstituted naphthalene.
Triazole includes substituted or unsubstituted triazole.
Tetrazole includes substituted or unsubstituted tetrazole.
Pyran includes substituted or unsubstituted pyran.
Thiapyran includes substituted or unsubstituted thiapyran.
Oxadiazole includes substituted or unsubstituted oxadiazole.
Triazine includes substituted or unsubstituted triazine.
Tetrazine includes substituted or unsubstituted tetrazine.
Carbazole includes substituted or unsubstituted carbazole.
Dibenzothiophene includes substituted or unsubstituted dibenzothiophene.
Dibenzofuran includes substituted or unsubstituted dibenzofuran.
Piperazine includes substituted or unsubstituted piperazine.
Piperidine includes substituted or unsubstituted piperidine.
Pyrrolidine includes substituted or unsubstituted pyrrolidine.

Emission of gold(III) compounds is rarely observed in contrast to the isoelectronic platinum(II) systems which are known to possess rich luminescence properties. The lack of luminescence in gold(III) compounds is probably due to the presence of low-lying d-d ligand field (LF) states as well as the electrophilicity of the gold(II) metal center. In order to enhance the luminescence of gold(III) compounds, it is believed that one could incorporate strong σ-donating ligands to the gold(III) metal center to make it more electron-rich, thereby raising the energy of the d-d LF states and thus increasing the chances for population of the emissive state. Gold(III) compounds with exceptionally interesting luminescence properties have been reported in the literature. For instance, a series of gold(III) aryl complexes was found to show interesting luminescence properties even at room temperature and were stable upon light irradiation [Yam et al. *J. Chem. Soc., Dalton Trans.* 1001 (1993)]. Later on, a class of luminescence biscyclometalated alkynylgold(III) complexes has been reported, in which strong σ-donating alkynyl groups have been incorporated into the gold(III) metal center to improve the emission properties. These complexes were found to be emissive at both room and low temperatures in various media [Yam et al. *Angew. Chem. Int. Ed.* 44, 3107 (2005); Wong et al. *J. Am. Chem. Soc.* 129, 4350 (2007)]. The use of such alkynylgold(III) compounds as electrophosphorescent emitters or dopants of organic light-emitting diodes (OLEDs) has recently been communicated in the literature [Wong et al. *Chem. Commun.* 2906 (2005)].

In addition to those gold(III) complex with tridentate cyclometalated ligands reported in US Pat. No. 2006/0091378 A1, the present invention will also employ various new gold(III) compounds as the light-emitting material for OLEDs. Furthermore, the design and composition of the organic electroluminescent device has been modified in the present invention, resulting in much improved OLED performance in terms of external quantum efficiencies.

The luminescent gold(III) compounds of the present invention can be formed into thin films by vacuum deposition, spin-coating, inkjet printing or other known fabrication methods. Different multilayer OLEDs have been fabricated using the compounds of the present invention as light-emitting material or as dopant in the emitting layer. In general, the OLEDs consist on an anode and a cathode, between which are the hole transporting layer, light-emitting layer, and electron transporting or injection layer. The present invention makes use of an additional carrier confinement layer to improve the performance of the devices.

Referring to FIG. 1, an organic EL device has, in order, a substrate, a hole-injecting anode, a hole transporting layer, a carrier confinement layer, a light-emitting layer, an electron transporting layer, and an electron-injecting cathode.

The substrate is electrically insulated and can be either optically transparent (e.g. glass or plastic foil) or opaque (e.g. semiconducting materials or ceramics). For viewing the EL emission through the substrate, or through both sides of the device, a glass substrate or a plastic foil is used. For applications where the EL emission is viewed through the top electrode, opaque semiconductor and ceramic wafers can be used.

The hole-injecting anode injects holes into the organic EL layer when this anode is positively biased. The anode is composed of a conductive and optionally transmissive layer. If the viewing of the EL emission through the substrate is desirable, the hole-injecting anode should be transparent. For applications where the EL emission is viewed through the top electrode, the transmissive characteristic of the anode is immaterial, and therefore any appropriate materials such as metals or metal compounds having a work function of greater than 4.1 eV can be used. Possible metals include gold, iridium, molybdenum, palladium, and platinum. If the anode should be transmissive, suitable materials can be selected from the group of metal oxides, including indium-tin oxide, aluminum- or indium-doped zinc oxide, tin oxide, magnesium-indium oxide, nickel-tungsten oxide, and cadmium-tin oxide. The desired metals and metal oxides can be deposited by evaporation, sputtering, laser ablation, and chemical vapor deposition.

The hole-transporting layer contains at least one hole-transporting aromatic tertiary amine. Suitable materials for use in the hole-transporting layer include 4,4'-bis[N-(1-naphthyl)-N-phenylamino]biphenyl (NPB), 4,4'-bis[N-(3-methylphenyl)-N-phenylamino]biphenyl (TPD), 4,4',4"-tris[(3-methylphenyl)phenylamino]triphenylaamine (MTDATA), and di-[4-(N,N-ditolyl-amino)phenyl]cyclohexane (TAPC). The carrier confinement layer is used to prevent the migration of triplet excitons out of the light-emitting layer. The carrier confinement layer should have the following features: i) the triplet energy must be sufficiently high to suppress the Dexter energy transfer from the phosphorescent triplet state of dopant material to a lower-lying, nonradiative triplet state of the hole-transporting material; ii) the hole-transporting properties and the highest occupied molecular orbital (HOMO) energy level should facilitate hole injection from the hole-transporting layer to the light-emitting layer; iii) the lowest unoccupied molecular orbital (LUMO) energy level should be above that of the host material in the light-emitting layer. Preferred materials for use in forming the carrier confinement layer are 4,4'-bis(carbazol-9-yl)biphenyl (CBP), m-(N,N'-dicarbazole)benzene (mCP) and 4,4',4"-tris(carbazol-9-yl)triphenylamine (TCTA). The light-emitting layer is formed by doping the phosphorescent Au(III) metal complex as a dopant into a host compound. Suitable host materials should be selected so that the triplet exciton can be transferred efficiently from the host material to the phosphorescent dopant material. Suitable host materials include certain aryl amines, triazoles and carbazole compounds. Examples of desirable hosts are CBP, mCP, TCTA, 3-(4-biphenylyl)-4-phenyl-5-tert-butylphenyl-1,2,4-triazole (TAZ), p-bis(triphenylsilyl)benzene (UGH2), and poly(N-vinylcarbazole) (PVK). The electron-transporting layer consists of materials or mixtures of materials which have a high ionization potential and wide optical band gap. Suitable electron-transporting materials include 1,3,5-tris(phenyl-2-benzimidazolyl)-benzene (TPBI), bathocuproine (BCP), bathophenanthroline (BPhen) and bis(2-methyl-8-quinolinolate)-4-(phenylphenolate)aluminum (BAlq). The organic film can be prepared by thermal evaporation, spin-coating, inkjet printing from a solution, or other known fabrication methods.

The top electron-injecting cathode acts as a transmissive electron injector that injects electrons into the organic EL layer when the cathode is negatively biased. The cathode is formed by a thin fluoride layer (which may be omitted) and a metal or metal alloy, preferably having a work function of less than 4 eV. Suitable materials include Mg:Ag, Li:Ag, Al.

The present invention will be illustrated more specifically by the following non-limiting examples, it being understood that changes and variations can be made therein without deviating from the scope and the spirit of the invention as hereinafter claimed. It is also understood that various theories as to why the invention works are not intended to be limiting.

The compounds described above have been represented throughout by their monomeric structure. As is well known to those in the art, the compounds may also be present as dimers, trimers, oligomers, polymers or dendrimers. For example, $R_1$ can be a donor ligand with a structure where two Au—C bonds can be formed between two different C atoms of $R_1$ and two different Au atoms. Alternately substituents can be bridging groups between two different rings A, B, or C or between one of the rings and $R_1$ where two or more monomeric structures are combined into a dimeric, trimeric oligomeric or polymeric structure.

Example 1

General Synthetic Methodology

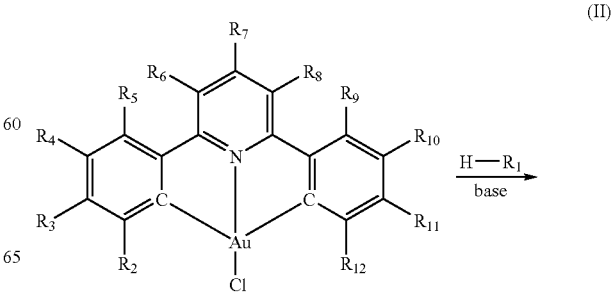

-continued

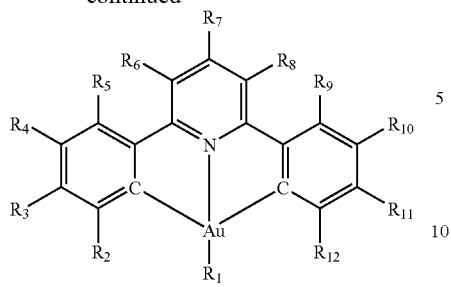

wherein:

(a) $R_1$ is selected from, but not limited to, alkylalkynyl, substituted alkylalkynyl, arylalkynyl, substituted arylalkynyl, heteroarylalkynyl, substituted heteroarylalkynyl and $(C{\equiv}C)_nR_{13}$, where $(C{\equiv}C)$ represents a carbon-carbon triple bond, n=1-8, and $R_{13}$ is selected from alkyl, aryl, substituted aryl, heteroaryl, substituted heteroaryl and tri(alkyl)silyl;

(b) $R_2$-$R_{12}$ groups are each independently selected from, but is not limited to, hydrogen, alkyl, alkenyl, alkynyl, alkylaryl, aryl and cycloalkyl with one or more alkyl, alkenyl, alkynyl, alkylaryl, cycloalkyl, OR, $NR_2$, SR, C(O)R, C(O)OR, $C(O)NR_2$, CN, $CF_3$, $NO_2$, $SO_4$, SOR, $SO_3R$, halo, aryl, substituted aryl, heteroaryl, substituted heteroaryl or a heterocyclic group.

As can be appreciated by those skilled in the art, the position, structure and size of the substituents $R_2$ through $R_{12}$ and any substituent included on $R_1$ are chosen to avoid steric inhibition of Au—C bond formation. In some embodiments of the invention $R_5$ and $R_6$ and/or $R_8$ and $R_9$ can be combined into a bridging group of two or more atoms that permit the planes of the pyridyl and phenyl rings to achieve the proper orientation for formation of the Au—C and Au—N bonds of compound (II).

Example 2

Synthesis and Characterization

Compounds 1, 2, 7 and 11 have been reported in the literature [Wong et al. *Chem. Commun.* 2906-2908 (2005); Wong et al., *J. Am. Chem. Soc.* 129, 4350 (2007)]. Compounds 3-6 and 8-10 were synthesized by a similar methodology, in which the tridentate ligands, 2,5-F₂Ph-C^N^C and FC^N^CF, and the precursor compounds, [Au(2,5-F₂Ph-C^N^C)Cl] and [Au(FC^N^CF)Cl], were respectively prepared according to modified literature procedures [Kröhnke, F. *Synthesis*, 1 (1976); Wong, K. H.; Cheung, K. K.; Chan, M. C. W.; Che, C. M. *Organometallics* 17, 5305 (1998)].

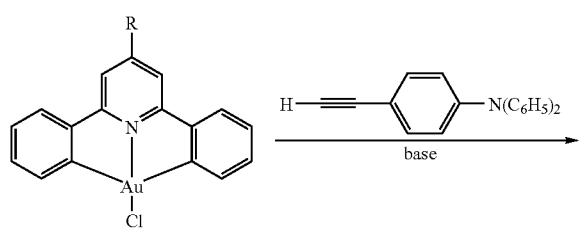

-continued

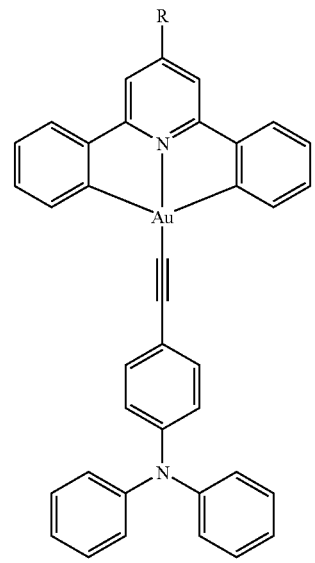

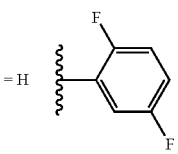

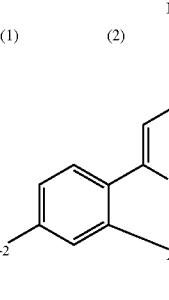

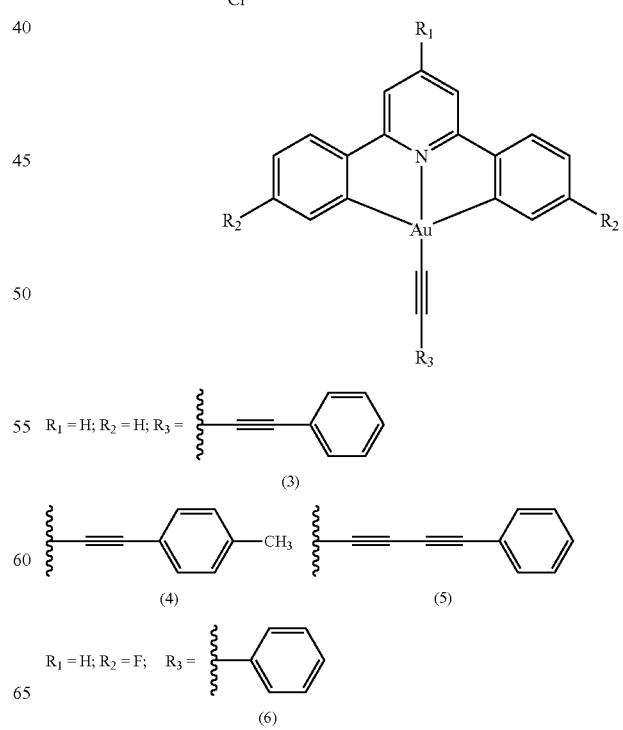

-continued

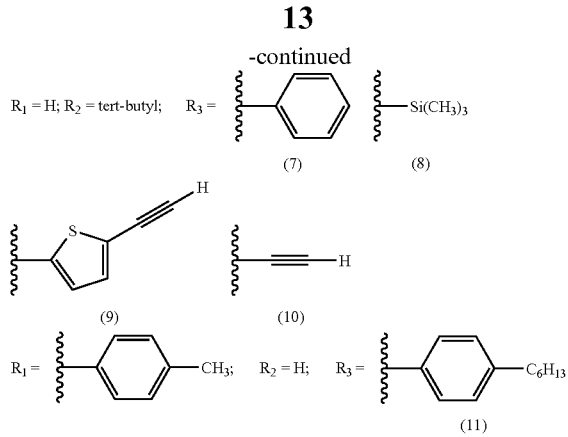

$R_1 = H; R_2 = \text{tert-butyl};$ (7) (8) (9) (10)

$R_1 =$ —C$_6$H$_4$—CH$_3$; $R_2 = H$; $R_3 =$ —C$_6$H$_4$—C$_6$H$_{13}$ (11)

Example 3

The characteristic spectroscopic properties of compounds 1-11 are as follows:

[Au(C^N^C)(C≡C—C$_6$H$_4$—N(C$_6$H$_5$)$_2$-p)]  (Compound 1)

Yield: 80%. $^1$H NMR (400 MHz, CD$_2$Cl$_2$, 298 K, relative to Me$_4$Si): δ 7.01-7.07 (m, 4H, C≡CC$_6$H$_4$ and NPh$_2$), 7.10-7.13 (m, 4H, NPh$_2$), 7.26-7.30 (m, 6H, phenyl of C^N^C and NPh$_2$), 7.40 (dt, J=7.3 and 1.2 Hz, 2H, phenyl of C^N^C), 7.46 (d, J=8.7 Hz, 2H, C≡CC$_6$H$_4$), 7.54 (d, J=8.0 Hz, 2H, pyridyl of C^N^C), 7.62 (dd, J=7.3 and 1.2 Hz, 2H, phenyl of C^N^C), 7.91 (t, J=8.0 Hz, 1H, pyridyl of C^N^C), 8.03 (dd, J=7.3 and 1.2 Hz, 2H, phenyl of C^N^C). Positive FAB-MS: m/z 694 [M]$^+$. IR (KBr disc): 2149 cm$^{-1}$ ν(C≡C). Elemental analyses: Found (%): C, 62.34; H, 3.55; N, 3.86. Calcd for C$_{37}$H$_{25}$AuN$_2$·H$_2$O: C, 62.36; H, 3.82; N, 3.93.

[Au(2,5-F$_2$-Ph-C^N^C)(C≡C—C$_6$H$_4$—N(C$_6$H$_5$)$_2$-p)]  (Compound 2)

Yield: 28%. $^1$H NMR (300 MHz, CD$_2$Cl$_2$, 298 K, relative to Me$_4$Si): δ7.06 (m, 4H, C≡CC$_6$H$_4$ and NPh$_2$), 7.10 (d, J=8.7 Hz, 4H, NPh$_2$), 7.24-7.30 (m, 8H, phenyl of C^N^C and NPh$_2$), 7.36-7.43 (m, 5H, C≡CC$_6$H$_4$ and phenyl of C^N^C), 7.63 (m, 4H, pyridyl and phenyl of C^N^C), 8.01 (d, J=6.1 Hz, 2H, phenyl of C^N^C). Positive FAB-MS: m/z 808 [M]$^+$. IR (KBr disc): 2153 cm$^{-1}$ ν(C≡C). Elemental analyses Found (%): C, 62.64; H, 3.33; N, 3.19. Calcd for C$_{43}$H$_{27}$N$_2$F$_2$Au·H$_2$O: C, 62.63; H, 3.54; N, 3.40.

[Au(C^N^C)(C≡C—C≡C—CC$_6$H$_5$)]  (Compound 3)

Yield: 82%. $^1$H NMR (400 MHz, CD$_2$Cl$_2$, 298 K, relative to Me$_4$Si): δ 7.29 (dt, J=7.4 and 1.3 Hz, 2H, phenyl of C^N^C), 7.35-7.37 (m, 3H, C≡CC$_6$H$_5$), 7.41 (dt, J=7.4 and 1.3 Hz, 2H, phenyl of C^N^C), 7.52 (d, J=8.0 Hz, 2H, pyridyl of C^N^C), 7.54-7.57 (m, 2H, C≡CC$_6$H$_5$), 7.61 (dd, J=7.4 and 1.3 Hz, 2H, phenyl of C^N^C), 7.90-7.96 (m, 3H, phenyl and pyridyl of C^N^C). Positive FAB-MS: 71/z 552 [M]$^+$. IR (KBr disc): 2095 and 2198 cm$^{-1}$, ν(C≡C). Elemental analyses: Found (%): C, 58.67; H, 3.01; N, 2.58. Calcd for C$_{27}$H$_{16}$NAu: C, 58.76; H, 2.90; N, 2.54.

[Au(C^N^C)(C≡C—C≡C—CC$_6$H$_4$—CH$_3$-p)]  (Compound 4)

Yield: 88%. $^1$H NMR (400 MHz, CD$_2$Cl$_2$, 298 K, relative to Me$_4$Si): δ2.37 (s, 3H, CH$_3$), 7.17 (d, J=8.0 Hz, 2H, C≡CC$_6$H$_4$), 7.21 (dt, J=7.6 and 1.3 Hz, 2H, phenyl of C^N^C), 7.33 (dt, J=7.6 and 1.3 Hz, 2H, phenyl of C^N^C), 7.44 (d, J=8.0 Hz, 2H, pyridyl of C^N^C), 7.45 (d, J=8.0 Hz, 2H, C≡CC$_6$H$_4$), 7.51 (dd, J=7.6 and 1.3 Hz, 2H, phenyl of C^N^C), 7.83-7.88 (m, 3H, phenyl and pyridyl of C^N^C). Positive FAB-MS: m/z 566 [M]$^+$. IR (KBr disc): 2080 and 2195 cm$^{-1}$ ν(C≡C). Elemental analyses: Found (%): C, 59.78; H, 3.24; N, 2.69. Calcd for C$_{18}$H$_{18}$NAu: C, 59.48; H, 3.21; N, 2.48.

[Au(C^N^C)(C≡C—C≡C—C≡CC$_6$H$_5$)]  (Compound 5)

Yield: 32%. $^1$H NMR (400 MHz, CD$_2$Cl$_2$, 298 K, relative to Me$_4$Si): δ 7.29 (dt, J=7.6 and 1.3 Hz, 2H, phenyl of C^N^C), 7.33-7.39 (m, 3H, C≡CC$_6$H$_5$), 7.41 (dt, J=7.6 and 1.3 Hz, 2H, phenyl of C^N^C), 7.52 (d, J=8.0 Hz, 2H, pyridyl of C^N^C), 7.54-7.57 (m, 2H, C≡CC$_6$H$_5$), 7.61 (dd, J=7.6 and 1.3 Hz, 2H, phenyl of C^N^C), 7.91 (dd, J=7.6 and 1.3 Hz, 2H, phenyl of C^N^C), 7.92 (t, J=8.0 Hz, 1H, pyridyl of C^N^C). Positive FAB-MS: m/z 576 [M]$^+$. IR (KBr disc): 2066 and 2155 cm$^{-1}$ ν(C≡C). Elemental analyses: Found (%): C, 60.73; H, 2.99; N, 2.50. Calcd for C$_{29}$H$_{16}$NAu: C, 60.53; H, 2.80; N, 2.43.

[Au(FC^N^CF)(C≡CC$_6$H$_5$)]  (Compound 6)

Yield: 78%. $^1$H NMR (400 MHz, CD$_2$Cl$_2$, 298 K, relative to Me$_4$Si): δ6.89 (dt, J=8.7 and 2.7 Hz, 2H, phenyl of FC^N^CF), 7.32-7.41 (m, 5H, pyridyl of FC^N^CF and C≡CC$_6$H$_5$), 7.56-7.61 (m, 4H, phenyl of FC^N^CF and C≡CC$_6$H$_5$), 7.65 (dd, J=8.7 and 2.7 Hz, 2H, phenyl of FC^N^CF), 7.85 (t, J=8.0 Hz, 1H, pyridyl of FC^N^CF). Positive FAB-MS: 71/Z 564 [M]$^+$. IR (KBr disc): 2151 cm$^{-1}$ ν(C≡C). Elemental analyses: Found (%): C, 53.02; H, 2.58; N, 2.65. Calcd for C$_{25}$H$_{14}$F$_2$NAu: C, 53.30; H, 2.50; N, 2.49.

[Au($^t$BuC^N^C$^t$Bu)(C≡CC$_6$H$_5$)]  (Compound 7)

Yield: 85%. $^1$H NMR (400 MHz, CD$_2$Cl$_2$, 298 K, relative to Me$_4$Si): δ 1.39 (s, 18H, $^t$Bu), 7.35 (m, 5H, C≡CC$_6$H$_5$), 7.46 (d, J=8.0 Hz, 2H, pyridyl of $^t$BuC^N^C$^t$Bu), 7.56 (d, J=8.2 Hz, 2H, phenyl of $^t$BuC^N^C$^t$Bu), 7.60 (dd, J=8.2 and 2.0 Hz, 2H, phenyl of $^t$BuC^N^C$^t$Bu), 7.86 (t, J=8.0 Hz, 1H, pyridyl of $^t$BuC^N^C$^t$Bu), 8.18 (d, J=2.0 Hz, 2H, phenyl of $^t$BuC^N^C$^t$Bu). Positive EI-MS: m/z 640 [M]$^+$. IR (KBr disc): 2149 cm$^{-1}$ ν(C≡C). Elemental analyses: Found (%): C, 61.02; H, 5.08; N, 2.17. Calcd for C$_{33}$H$_{32}$NAu·½H$_2$O: C, 61.11; H, 5.09; N, 2.16.

[Au($^t$BuC^N^C$^t$Bu)(C≡CSiMe$_3$)]  (Compound 8)

Yield: 82%. $^1$H NMR (400 MHz, CDCl$_3$, 298 K, relative to Me$_4$Si): δ 0.29 (s, 9H, SiMe$_3$), 1.37 (s, 18H, $^t$Bu), 7.30 (dd, J=8.1 and 2.0 Hz, 2H, phenyl of $^t$BuC^N^C$^t$Bu), 7.44 (d, J=8.0 Hz, 2H, pyridyl of $^t$BuC^N^C$^t$Bu), 7.54 (d, J=8.1 Hz, 2H, phenyl of $^t$BuC^N^C$^t$Bu), 7.84 (t, J=8.0 Hz, 1H, pyridyl of $^t$BuC^N^C$^t$Bu), 8.07 (d, J=2.0 Hz, 2H, phenyl of $^t$BuC^N^C$^t$Bu). Positive FAB-MS: m/z 636 [M]$^+$. IR (KBr disc): 2085 cm$^{-1}$ ν(C≡C). Elemental analyses: Found (%): C, 56.78; H, 5.81; N, 2.12. Calcd for C$_{30}$H$_{36}$NSiAu: C, 56.68; H, 5.71; N, 2.20.

[Au($^t$BuC^N^C$^t$Bu)(C≡CC$_4$H$_4$C≡CH)]  (Compound 9)

Yield: 70%. $^1$H NMR (300 MHz, CDCl$_3$, 298 K, relative to Me$_4$Si): δ1.39 (s, 18H, $^t$Bu), 3.34 (s, 1H, acetylene), 7.08 (d, J=3.8 Hz, 1H, thienyl), 7.16 (d, J=3.8 Hz, 1H, thienyl), 7.29 (dd, J=8.1 Hz and 1.9 Hz, 2H, phenyl of $^t$BuC^N^C$^t$Bu), 7.41 (d, J=8.1 Hz, 2H, pyridyl of $^t$BuC^N^C$^t$Bu), 7.51 (d, J=8.1 Hz, 2H, phenyl of $^t$BuC^N^C$^t$Bu), 7.82 (t, J=8.1 Hz, 1H, pyridyl of $^t$BuC^N^C$^t$Bu), 8.14 (d, 2H, J=1.9 Hz, phenyl of $^t$BuC^N^C$^t$Bu). Positive FAB-MS: m/z 670 [M]$^+$. IR (KBr disc): 2092 and 2148 cm$^{-1}$ ν(C≡C). Elemental analyses: Found (%): C, 58.72; H, 4.52; N, 2.09. Calcd for C$_{33}$H$_{30}$NSF$_2$Au·½CH$_3$OH: C, 58.68; H, 4.70; N, 2.04.

[Au($^t$BuC^N^C$^t$Bu)(C≡C—C≡CH)]  (Compound 10)

Yield: 63%. $^1$H NMR (400 MHz, CD$_2$Cl$_2$, 298 K, relative to Me$_4$Si): δ 1.37 (s, 18H, $^t$Bu), 2.15 (s, 1H, C≡CH), 7.31

(dd, J=8.2 and 2.1 Hz, 2H, phenyl of 'BuC^N^C'Bu), 7.42 (d, J=8.0 Hz, 2H, pyridyl of 'BuC^N^C'Bu), 7.51 (d, J=8.2 Hz, 2H, phenyl of 'BuC^N^C'Bu), 7.84 (t, J=8.0 Hz, 1H, pyridyl of 'BuC^N^C'Bu), 7.99 (d, J=2.1 Hz, 2H, phenyl of 'BuC-^N^C'Bu). Positive FAB-MS: m/z 588 [M]+. IR (KBr disc): 2058 and 2181 cm$^{-1}$ ν(C≡C). Elemental analyses: Found (%): C, 59.15; H, 4.90; N, 2.61. Calcd for $C_{29}H_{28}NAu$: C, 59.29; H, 4.80; N, 2.38.

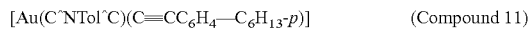
(Compound 11)

Yield: 80%. $^1$H NMR (300 MHz, $CD_2Cl_2$, 298 K, relative to $Me_4Si$): δ 0.91 (t, J=6.8 Hz, 3H, $CH_3$), 1.34 (m, 6H, $CH_2$), 1.62-1.64 (m, 2H, $CH_2$), 2.46 (s, 3H, $CH_3$ of tolyl), 2.64 (t, J=7.7 Hz, 2H, $CH_2$), 7.17 (d, J=8.0 Hz, 2H, C≡$CC_6H_4$), 7.27 (dt, J=7.5 and 1.0 Hz, 2H, phenyl of C^N(Tol)^C), 7.35-7.40 (m, 4H, phenyl of C^N(Tol)^C and pyridyl of C^N(Tol)^C), 7.47 (d, J=8.0 Hz, 2H, C≡$CC_6H_4$), 7.66-7.71 (m, 6H, phenyl of C^N(Tol)^C and tolyl), 8.01 (dd, J=7.5 and 1.0 Hz, 2H, phenyl of C^N(Tol)^C). Positive FAB-MS: m/z 703 [M]+. IR (KBr disc): 2142 cm$^{-1}$ ν(C≡C). Elemental analyses: Found (%): C, 64.74; H, 4.87; N, 1.92. Calcd for $C_{38}H_{34}NAu$: C, 64.99; H, 4.85; N, 2.00.

Example 4

UV-Vis Absorption Properties

Gold(III) compounds of the present invention can exhibit rich luminescence at both room temperature and low temperature in various media. In particular, measurements demonstrate that the compounds show intense photoluminescence in dichloromethane solution at 298 K. The photophysics of compounds 1, 2, 7 and 11 have been reported [Wong et al. Chem. Commun. 2906-2908 (2005); Wong et al. J. Am. Chem. Soc. 129, 4350-4365 (2007)], whereas the photophysical data of selected compounds are summarized in Table 1.

Figure 2:
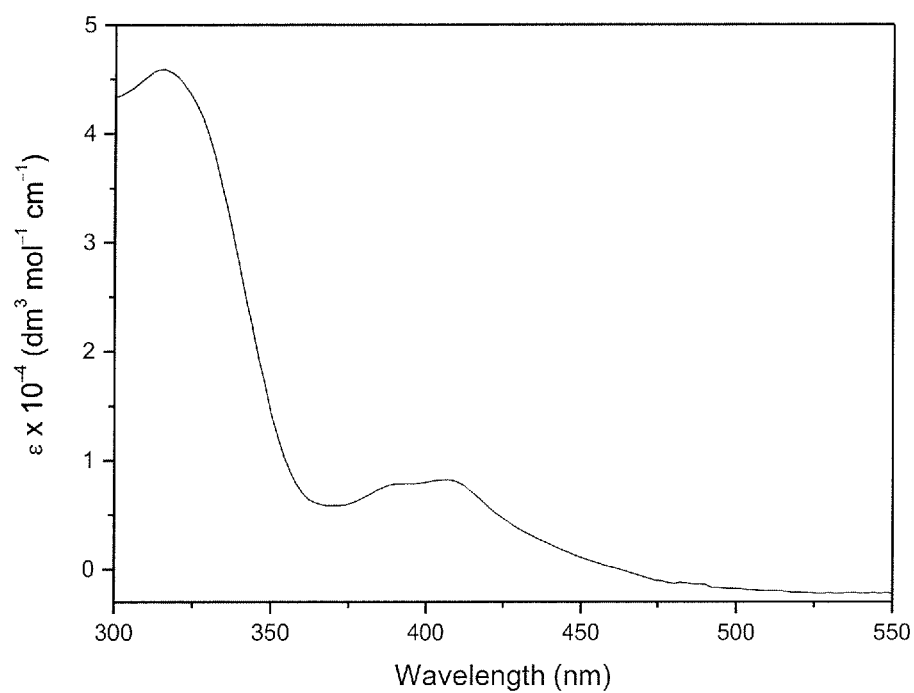
FIG. 2 shows the UV-vis absorption spectrum of compound 2 in dichloromethane at 298 K.

As shown in FIG. 2, compound 2 exhibits an intense absorption band at ca. 316 nm and a moderately intense vibronic-structured absorption band at 390-410 nm in dichloromethane at 298 K. The low-energy vibronic-structured absorption band shows vibrational progressional spacings of ca. 1250 cm$^{-1}$, corresponding to the skeletal vibrational frequency of the C^N^C ligand. The low-energy absorptions are assigned as intraligand (IL) π-π* transition of the C^N^C ligand.

Figure 3:
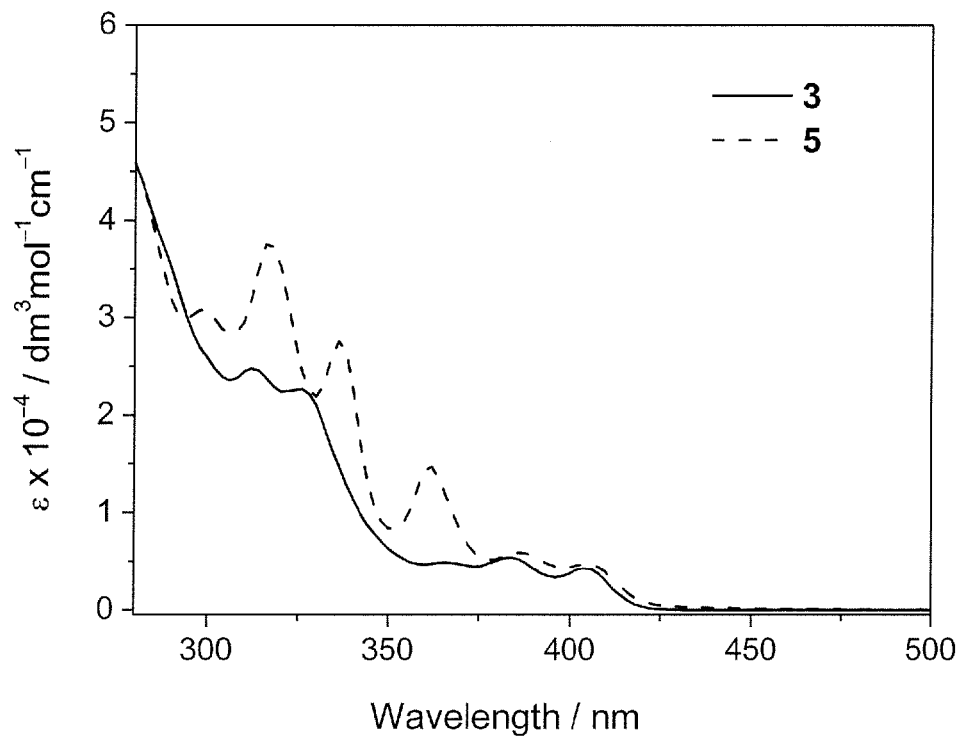
FIG. 3 shows the UV-vis absorption spectra of compounds 3 and 5 in dichloromethane at 298 K.

As shown in FIG. 3, compounds 3 and 5 show low-energy vibronic-structured absorption bands at ca. 362-412 nm in their electronic absorption spectra in dichloromethane at room temperature. Similar to other monoynyl analogues, such low-energy absorption band was tentatively assigned as the metal-perturbed IL [π→π*(RC^N^CR)] transition, involving some charge transfer from the phenyl moiety to the pyridyl unit. It is noteworthy that the electronic absorption spectrum of 5 in dichloromethane featured additional highly vibronic-structured absorption bands at 298-362 nm with vibrational progressional spacings of ca. 2020 cm$^{-1}$, which were typical of the ν(C≡C) stretching frequency. By comparing the absorption spectrum with that of the free ligand 1-(hexa-1,3,5-triynyl)benzene, the absorptions in 5 were assigned as an admixture of the metal-perturbed IL [π→π* (C^N^C)] and IL [π→π*(C≡C)] transitions.

Example 5

Photoluminescence Properties

In contrast to most other Au(III) compounds which are non-emissive or only show luminescence at low temperature, the compounds display intense luminescence at 450-665 nm in the solution state at room temperature (Table 1).

Figure 4:
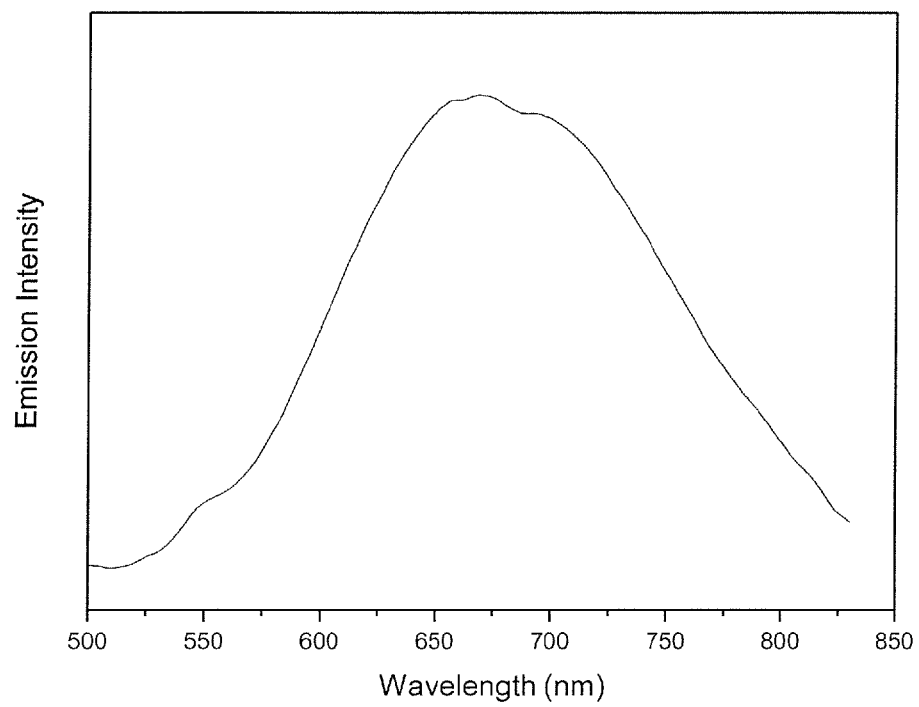
FIG. 4 shows the emission spectrum of compound 2 in dichloromethane at 298 K. No instrumental correction was applied for the emission wavelength.

FIG. 4 shows the emission spectrum of compound 2 in dichloromethane at room temperature. In addition to an intense emission band at ca. 450 nm, a broad structureless emission band is observed at ca. 665 nm. With reference to the spectroscopic studies on the emission properties of related compounds, this low-energy structureless band is assigned as derived from an excited state of $^3$LLCT [π(C≡$CC_6H_4$N $(C_6H_5)_2$)→π*(C^N^C)] origin due to the presence of energetically higher-lying π(C≡$CC_6H_4$N$(C_6H_5)_2$) orbital resulting from the strong electron-donating substituent.

Figure 5:
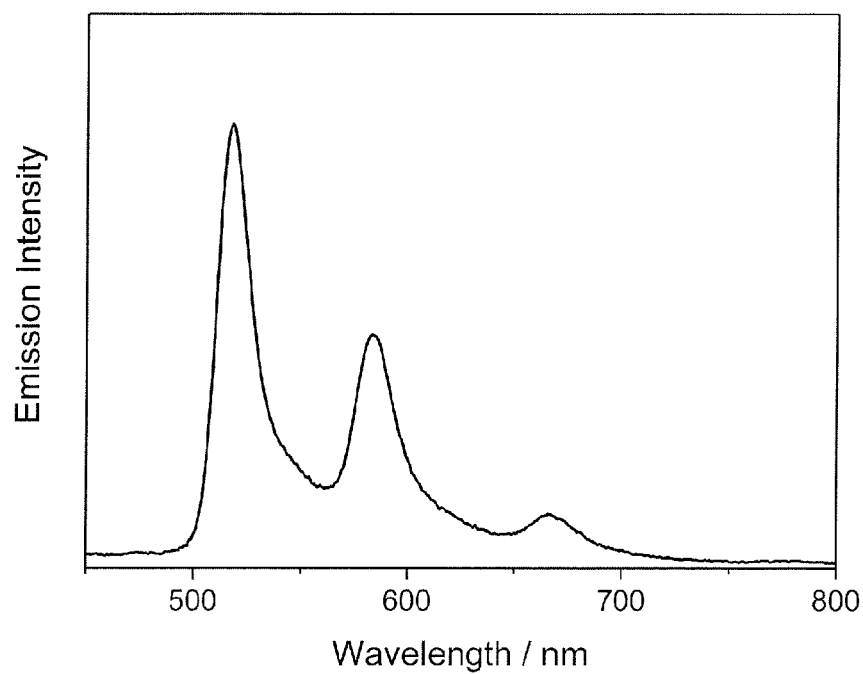
FIG. 5 shows the emission spectra of 5 in degassed dichloromethane at 298 K. No instrumental correction was applied for the emission wavelength.

FIG. 5 shows the emission spectrum of mononuclear gold (III) triynyl complex 5 in dichloromethane at room temperature, in which a highly structured and narrow-bandwidth emission bands at ca. 518 nm is observed. The vibrational progressional spacings of ca. 2100 cm$^{-1}$ were characteristic of the ν(C≡C) stretches in the ground state, indicating the involvement of the hexatriynyl moiety in the excited state. It was likely that upon increasing the π conjugation of the carbon chains in 5, the origin of the emission changed in character, with an enhanced participation of the alkynyl unit in the emissive state, leading to an emission that was predominantly originating from a $^3$IL [π→π*(C≡C)$_3$] excited state of the hexatriynyl moiety.

TABLE 1

Photophysical data for selected compounds

| Compound | Medium (T/K) | Absorption $\lambda_{max}$/nm ($\epsilon_{max}$/dm$^3$mol$^{-1}$cm$^{-1}$) | Emission $\lambda_{max}$/nm |
| --- | --- | --- | --- |
| 1 | CH$_2$Cl$_2$ (298) | 320 (38270), 384 (9560), 400 (9565), 416 sh (5590) | 620 |
| 2 | CH$_2$Cl$_2$ (298) | 316 (45915), 390 (7810), 408 (8240) | 450, 665 |
| 3 | CH$_2$Cl$_2$ (298) | 312 (24750), 326 (22650), 366 (4710), 384 (5190), 404 (4130) | 478, 510, 556, 591 |
| 4 | CH$_2$Cl$_2$ (298) | 310 (21050), 324 (18360), 365 (5025), 383 (4875), 404 (3610) | 476, 508, 553, 595 |
| 5 | CH$_2$Cl$_2$ (298) | 298 (32095), 316 (38840), 336 (28500), 362 (15590), 386 (5400), 406 (4320) | 518, 584, 667 |
| 6 | CH$_2$Cl$_2$ (298) | 306 (13350), 316 (13085), 366 (3330), 384 (4190), 404 (3870) | 475, 505, 545, 585 |

TABLE 1-continued

Photophysical data for selected compounds

| Compound | Medium (T/K) | Absorption $\lambda_{max}$/nm ($\epsilon_{max}$/dm$^3$mol$^4$cm$^4$) | Emission $\lambda_{max}$/nm |
|---|---|---|---|
| 7 | CH$_2$Cl$_2$ (298) | 313 (26190), 323 (24460), 372 (6130), 392 (8035), 412 (7465) | 484, 514, 548, 593 |
| 8 | CH$_2$Cl$_2$ (298) | 314 (13620), 322 (12435), 376 (4010), 396 (5710), 416 (5470) | 486, 516, 556, 595 |
| 10 | CH$_2$Cl$_2$ (298) | 313 (14480), 322 (12810), 374 (3800), 394 (5775), 414 (5675) | 487, 520, 564, 636 |
| 11 | CH$_2$Cl$_2$ (298) | 290 (42660), 304 (40780), 330 (25220), 364 (6100), 386 (5120), 406 (3540) | 475, 505, 547, 592 |

Example 6

Construction of an Organic EL Device

An organic EL device according to an embodiment of the invention was constructed in the following manner:
a) a transparent anode ITO-coated glass substrate was ultrasonicated in a commercial detergent, rinsed in deionized water, and then dried in an oven. The substrate was further subjected to an UV-ozone treatment for 15 minutes;
b) the substrate was put into a vacuum chamber, and the chamber was pumped down to 5×10$^{-6}$ mbar;
c) a 70 nm thick NPB hole-transporting layer was deposited on ITO-coated glass substrate;
d) a 30 nm thick doped CBP light-emitting layer was deposited on CBP layer, in which 6% v/v compound 1 was doped into light-emitting CBP layer;
e) a 30 nm thick BAlq electron-transporting layer was deposited on doped CBP light-emitting layer;
f) a 0.8 nm thick LiF and a 80 nm thick Al were deposited on the BAlq layer as electron-injecting cathode.

All materials were prepared by thermal evaporation from tantalum boats. Deposition rates were monitored with a quartz oscillation crystal and controlled at 0.1-0.2 nm/s for both organic and metal layers. Current density-voltage-luminance characteristics of organic EL devices were measured with a programmable Keithley model 237 power source and a Spectrascan PR 650 photometer under ambient air conditions.

Example 7

Construction of Another Organic EL Device

The same materials and processing procedures were employed as described in Example 6, except that a 5 nm thick carrier confinement CBP layer was inserted in between the hole transporting layer and the light-emitting layer.

Figure 6:
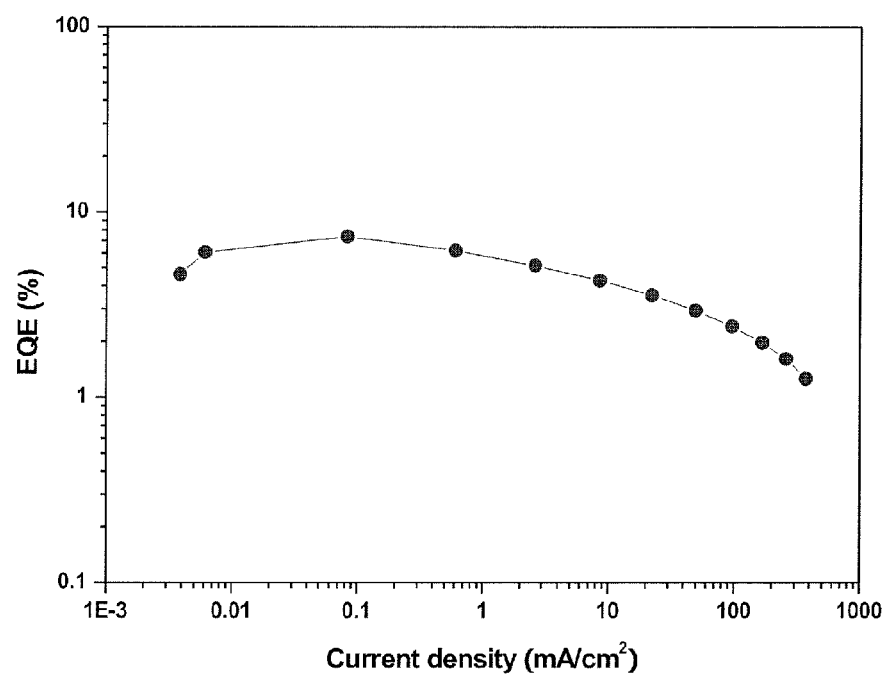
FIG. 6 shows the external quantum efficiency of device with the structure of ITO/NPB (70 nm)/6% compound 1:CBP (30 nm)/BAlq (30 nm)/LiF (0.8 nm)/Al (80 nm).
Figure 7:
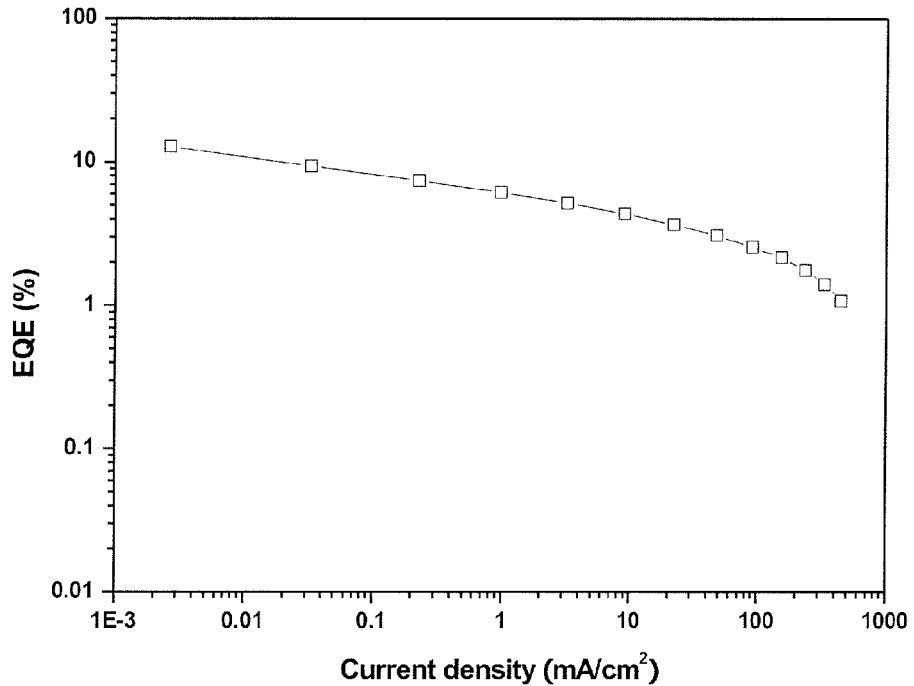
FIG. 7 shows the external quantum efficiency of device with the structure of ITO/NPB (70 nm)/CBP (5 nm)/6% compound 1:CBP (30 nm)/BAlq (30 nm)/LiF (0.8 nm)/Al (80 nm), in which the CBP layer is used as the carrier confinement layer.

FIG. 6 and FIG. 7 depict the plot of external quantum efficiencies of devices of Example 6 and 7, respectively. Without the carrier confinement layer, the device shows a maximum external quantum efficiency of 7.4%. On the other hand, a remarkable increase in device performance can be achieved by employing a carrier confinement layer, in which such device shows a maximum external quantum efficiency of 12.8%. This confirms that the carrier confinement layer between the hole transporting layer and the light emitting layer can effectively suppress the Dexter energy transfer from the phosphorescent triplet state of dopant material to the triplet state of hole-transporting material.

Example 8

Construction of Yet Another Organic EL Device

An organic EL device according to an embodiment of the invention was constructed in the following manner:
a) a transparent anode ITO-coated glass substrate was ultrasonicated in a commercial detergent, rinsed in deionized water, and then dried in an oven. The substrate was further subjected to an UV-ozone treatment for 15 minutes;
b) the substrate was put into a vacuum chamber, and the chamber was pumped down to 5×10$^{-6}$ mbar;
c) a 70 nm thick NPB hole-transporting layer was deposited on ITO-coated glass substrate;
d) a 5 nm thick CBP carrier confinement layer was deposited on NPB layer;
e) a 30 nm thick doped CBP light-emitting layer was deposited on CBP layer, in which 2, 4, 6, 8, and 10% v/v compound 2 was doped into light-emitting CBP layer;
f) a 30 nm thick BAlq electron-transporting layer was deposited on doped CBP light-emitting layer;
g) a 0.8 nm thick LiF and a 80 nm thick Al were deposited on the BAlq layer as electron-injecting cathode.

All materials were prepared by thermal evaporation from tantalum boats. Deposition rates were monitored with a quartz oscillation crystal and controlled at 0.1-0.2 nm/s for both organic and metal layers. Current density-voltage-luminance characteristics of organic EL devices were measured with a programmable Keithley model 237 power source and a Spectrascan PR 650 photometer under ambient air conditions.

Figure 8:
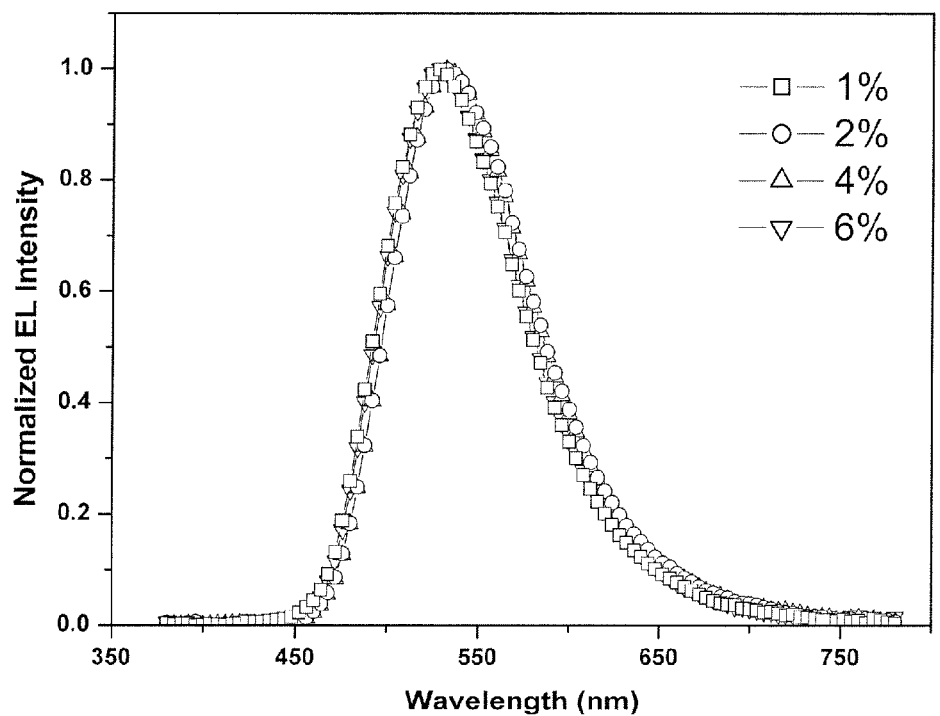
FIG. 8 shows the electroluminescence spectra of device of Example 3.

FIG. 8 depicts the EL spectra for devices of Example 8, in which y denotes the concentration of compound 2 doped into a CBP host material. Remarkably, pure green light emission was obtained from all devices with a dominating peak at 532 nm with a full spectral width at half maximum (FWHM) of 88±2 nm. It is worth noting that all devices exhibit nearly identical CIE coordinates of (0.34, 0.58). In addition, the EL spectra for all devices are almost independent of the driving voltage, with the FWHM remained unchanged over a wide luminance range. It suggests that the hole and electron recombination is well confined within the compound 2:CBP layer.

Figure 9:
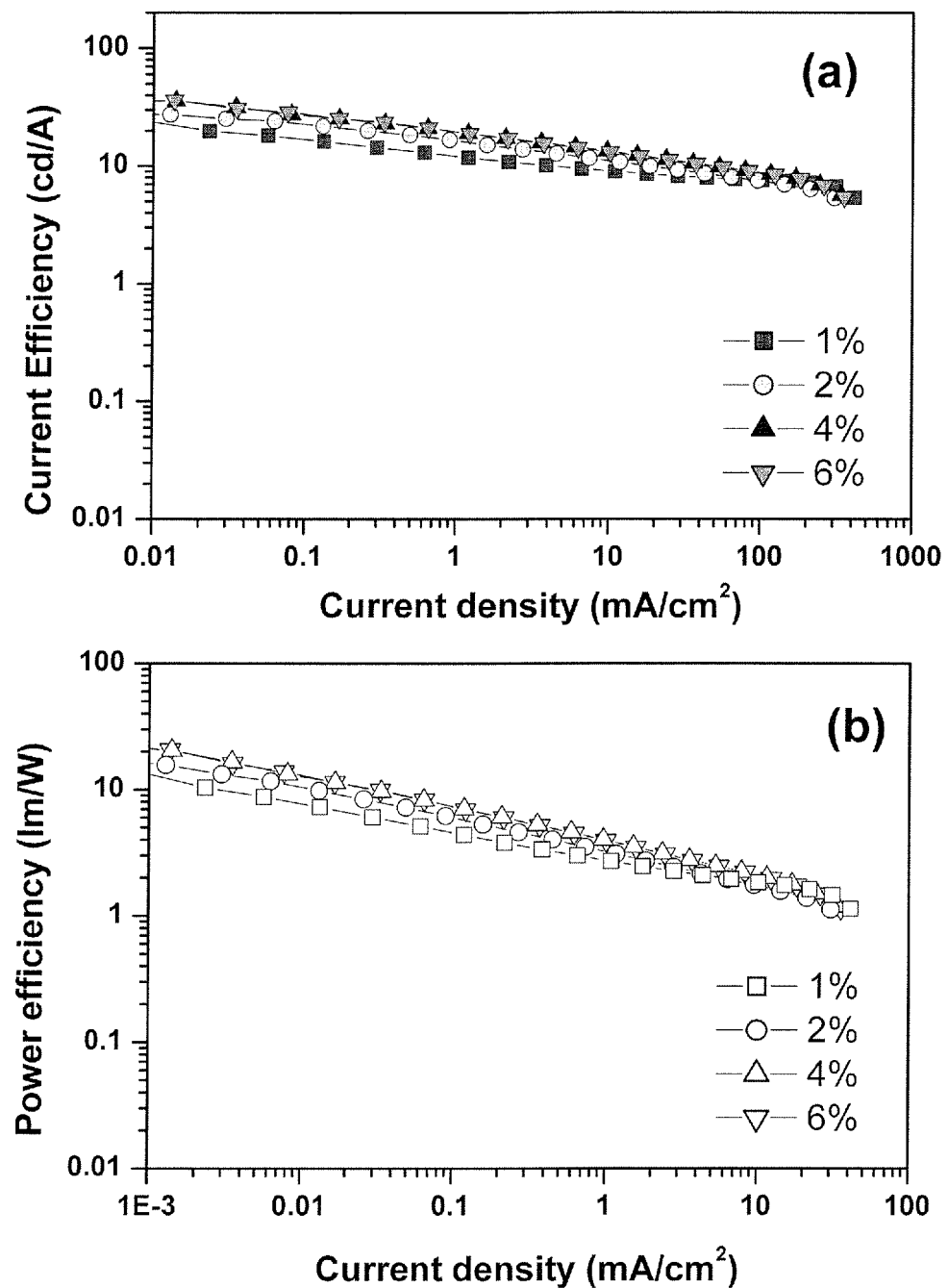
FIG. 9 shows a) current efficiency and b) power efficiency of devices of Example 3.

FIG. 9 shows the plot of a) current efficiency and b) power efficiency of devices of Example 8. At an optimized concentration of 4%, device exhibited high current efficiency of 36.0

What is claimed is:

1. A compound having the chemical structure represented by the following general formula (I),

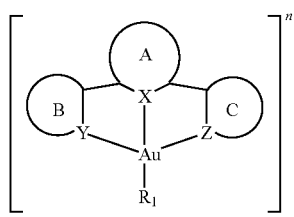

wherein:
(a) X is nitrogen;
(b) Y and Z are carbon;
(c) A is a pyridine group or a substituted pyridine;
(d) B and C are phenyl groups or substituted phenyl groups;
(e) $R_1$ is an optionally substituted carbon donor ligand attached to the gold atom;
(f) n is zero, a positive integer or a negative integer.

2. The compound of claim 1, wherein $R_1$ is selected from alkylalkynyl, substituted alkylalkynyl, arylalkynyl, substituted arylalkynyl, heteroarylalkynyl and substituted heteroarylalkynyl.

3. The compound of claim 1, wherein one or both of the rings B and C are fused with the ring A to form a polycyclic aromatic group.

4. The compound of claim 1, wherein two, three or more of the compounds are connected through a bridging substituent as a dimer, trimer, oligomer or polymer.

5. A compound having the chemical structure represented by the following general formula (II),

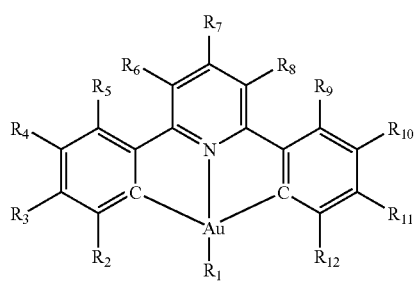

wherein:
(a) $R_1$ is selected from alkylalkynyl, substituted alkylalkynyl, arylalkynyl, substituted arylalkynyl, heteroarylalkynyl, substituted heteroarylalkynyl and $(C\equiv C)_n R_{13}$, where $(C\equiv C)$ represents a carbon-carbon triple bond, n=1–8, and $R_{13}$ is selected from alkyl, aryl, substituted aryl, heteroaryl, substituted heteroaryl and tri(alkyl)silyl; and
(b) $R_2$-$R_{12}$ groups are each independently a substituent.

6. A compound according to claim 5 wherein the groups $R_5$ and $R_6$ and/or $R_8$ and $R_9$ are combined into a bridging group of two or more atoms.

7. A compound according to claim 5 wherein the compound can be deposited as a thin layer.

8. A compound according to claim 7 wherein the thin layer can be deposited by sublimation, vacuum deposition, spin-coating, or inkjet printing.

9. A compound according to claim 5, wherein the compound has photoluminescence properties.

10. A compound according to claim 5, wherein the compound has electroluminescence properties.

11. A compound of claim 5, wherein the compound can be fabricated into a light-emitting device.

12. A compound of claim 5, wherein the compound serves as the light-emitting layer of a light-emitting device.

13. A compound of claim 5, wherein the compound serves as a dopant in the light-emitting layer of a light-emitting device.

14. A compound of claim 13 wherein luminescent energy of the compound varies with the concentration of the dopant.

15. A light-emitting device comprising a layer of the compound of claim 5.

16. A dopant comprising a compound according to claim 5.

17. A light-emitting device with structure of anode/hole-transporting layer/carrier confinement layer/light-emitting layer/electron-transporting layer/cathode wherein the light-emitting layer comprises the compound of claim 5.

18. A light-emitting device with structure of anode/hole-transporting layer/carrier confinement layer/light-emitting layer/electron-transporting layer/cathode, wherein the light-emitting layer comprises the compound of claim 5, wherein a carrier confinement layer that has a triplet energy higher than that of the compound of claim 5 is inserted between the hole-transporting layer and the light-emissive layer.

19. The compound of claim 1, wherein ring A is pyridine or substituted pyridyl with one or more substituents selected from alkyl, alkenyl, alkynyl, alkylaryl, cycloalkyl, CN, $CF_3$, $NO_2$, $SO_2$, halo, aryl, substituted aryl, heteroaryl, substituted heteroaryl or heterocyclic group.

20. The compound of claim 1, wherein rings B and C are benzene or substituted phenyl with one or more substituents selected from alkyl, alkenyl, alkynyl, alkylaryl, cycloalkyl, CN, $CF_3$, $NO_2$, $SO_2$, halo, aryl, substituted aryl, heteroaryl, substituted heteroaryl or heterocyclic group.

21. A compound according to claim 5, wherein $R_2$-$R_{12}$ groups are each independently selected from hydrogen, alkyl, alkenyl, alkynyl, alkylaryl, aryl and cycloalkyl with one or more alkyl, alkenyl, alkynyl, alkylaryl, cycloalkyl, CN, $CF_3$, $NO_2$, $SO_2$, halo, aryl, substituted aryl, heteroaryl, substituted heteroaryl or a heterocyclic group.

* * * * *

UNITED STATES PATENT AND TRADEMARK OFFICE
CERTIFICATE OF CORRECTION

PATENT NO. : 8,415,473 B2
APPLICATION NO. : 12/494765
DATED : April 9, 2013
INVENTOR(S) : Vivian Wing-Wah Yam et al.

It is certified that error appears in the above-identified patent and that said Letters Patent is hereby corrected as shown below:

In the Specification:

Column 11,
Line 27, "$SO_4$," should read --$SO_2$,--.

Column 13,
Line 54, "Positive FAB-MS: 71/z 552 [M]$^+$" should read
--Positive FAB-MS: $m/z$ 552 [M]$^+$--.

Column 14,
Lines 2-3, " for $C_{18}H_{18}NAu$: C, 59.48; H, 3.21; N, 2.48" should read
-- for $C_{28}H_{18}NAu$: C 59.48, H 3.21, N 2.48 --.
Lines 24-25, "Positive FAB-MS: 71/Z 564 [M]$^+$" should read
--Positive FAB-MS: $m/z$ 564 [M]$^+$--.
Line 41, "$CDCl_2$, 298K" should read --CD2Cl2, 298 K--.
Line 52, Compound 9, " [Au($^t$BuC^N^C$^t$Bu)(C≡C$C_4H_4$C≡CH)]" should read
-- [Au($^t$BuC^N^C$^t$Bu)(C≡C$C_4H_4$SC≡CH)] --.

Signed and Sealed this
Twenty-fourth Day of September, 2013

Teresa Stanek Rea
*Deputy Director of the United States Patent and Trademark Office*